(12) United States Patent
Myklebust

(10) Patent No.: US 7,774,054 B2
(45) Date of Patent: Aug. 10, 2010

(54) METHOD AND SYSTEM TO DETERMINE CORRECT TUBE PLACEMENT DURING RESUSCITATION

(75) Inventor: Helge Myklebust, Stavanger (NO)

(73) Assignee: Laerdal Medical AS, Stavanger (NO)

( * ) Notice: Subject to any disclaimer, the term of this patent is extended or adjusted under 35 U.S.C. 154(b) by 678 days.

(21) Appl. No.: 11/180,724

(22) Filed: Jul. 14, 2005

(65) Prior Publication Data

US 2006/0011203 A1    Jan. 19, 2006

(30) Foreign Application Priority Data

Jul. 15, 2004    (NO) ................... 20043033

(51) Int. Cl.
| | |
|---|---|
| A61B 5/05 | (2006.01) |
| A61B 5/08 | (2006.01) |
| A61M 16/00 | (2006.01) |

(52) U.S. Cl. .................. 600/547; 600/529; 128/200.26
(58) Field of Classification Search ............... 600/547
See application file for complete search history.

(56) References Cited

U.S. PATENT DOCUMENTS

| | | | |
|---|---|---|---|
| 4,403,215 A | 9/1983 | Hofmann et al. | |
| 4,449,537 A | 5/1984 | Pross et al. | |
| 4,540,002 A | 9/1985 | Atlas | |
| 5,807,270 A | 9/1998 | Williams | |
| 6,351,671 B1 | 2/2002 | Myklebust | |
| 2002/0032383 A1 | 3/2002 | Weil et al. | |
| 2005/0256422 A1 * | 11/2005 | Wik ......................... 600/547 | |

FOREIGN PATENT DOCUMENTS

| | | |
|---|---|---|
| EP | 0 747 005 A1 | 12/1996 |
| EP | 1 073 310 | 7/1999 |
| EP | 1 057 451 | 5/2000 |
| EP | 1 057 498 | 5/2000 |
| EP | 1 157 717 | 5/2000 |
| EP | 1 215 993 | 9/2000 |
| EP | 1 079 310 | 2/2001 |
| WO | 89/07415 A1 | 8/1989 |
| WO | WO 2004/004541 | 6/2003 |
| WO | WO 2004/049942 | 12/2003 |
| WO | WO 2005/046431 | 5/2005 |

OTHER PUBLICATIONS

PCT International Search Report dated Oct. 11, 2005.

(Continued)

*Primary Examiner*—Patricia C Mallari
(74) *Attorney, Agent, or Firm*—Nixon & Vanderhye P.C.

(57) ABSTRACT

System and method for controlling insertion of a tracheal tube in a patient, comprising at least two electrodes adapted to be coupled to the patients chest for providing impedance measurements, a measuring instrument for performing the impedance measurement, said instrument also being provided with storage means for storing a first data set representing chosen characteristics of the impedance change during a first measurement, and evaluation means for comparing the first data set with a second data set representing the characteristics of a second impedance measurement, for evaluating the difference between said measurements and providing an evaluation signal, said first and second data sets representing impedance variations measured during lung inflation with and without an inserted tracheal tube.

20 Claims, 4 Drawing Sheets

OTHER PUBLICATIONS

Mehta K.H. et al; "An Assessment of the Ability of Impedance Respirometry Distinguish Oesophageal from Tracheal Intubation"; Anaesthesia; vol. 57, No. 11, Nov. 2002 pp. 1090-1093, XP002346548.

Heidenreich et al.; "Uninterrupted Chest Compression CPR Is Easier to Perform and Remember than Standard CPR"; Academic Emergency Medicine vol. 11, No. 5; 601; Abstract from 2004 Society of Academic Emergency Medicine Annual Meeting May 16-19, 2004.

Abu-Laban et al.; "A Comparison of Methodologic Approaches to Quantify Return of Spontaneous Circulation (ROSC) in Cardiac Arrest Research Including ROSC Survival Analysis"; Academic Emergency Medicine vol. 11, No. 5; 601-602; Abstract from 2004 Society of Academic Emergency Medicine Annual Meeting May 16-19, 2004.

Abu-Laban et al.; "Validation of the Gothenburg Futility Criteria for Out-of-Hospital Cardiac Arrest Presenting with Pulseless Electrical Activity"; Academic Emergency Medicine vol. 11, No. 5; 602; Abstract from 2004 Society of Academic Emergency Medicine Annual Meeting May 16-19, 2004.

Abu-Laban et al.; "Relationship between Rapicity of Fibrinolytic Administration and Probability of Pulse Return in Patients Given Tissue Plasminogen Activator during Pulseless Electrical Activity Cardiac Arrest"; Academic Emergency Medicine vol. 11, No. 5; 602-603; Abstract from 2004 Society of Academic Emergency Medicine Annual Meeting May 16-19, 2004.

Abella et al.; "Chest Compression Rates during CPR are Suboptimal: A Prospective Study during In-hospital Cardiac Arrest"; Academic Emergency Medicine vol. 11, No. 5; 603; Abstract from 2004 Society of Academic Emergency Medicine Annual Meeting May 16-19, 2004.

Rittenberger et al.; "BLS Performance Decreases with Increasing Resuscitation Complexity"; Academic Emergency Medicine vol. 11, No. 5; 603; Abstract from 2004 Society of Academic Emergency Medicine Annual Meeting May 16-19, 2004.

Larabee et al.; "Combination Pharmacotherapy vs. Standard Advanced Cardiac Life Support for the Treatment of Ventricular Fibrillation"; Academic Emergency Medicine vol. 11, No. 5; 603-604; Abstract from 2004 Society of Academic Emergency Medicine Annual Meeting May 16-19, 2004.

Vilke et al.; "The Three-phase Model of Cardiac Arrest as Applied to Ventricular Fibrillation in a Large, Urban Emergency Medical Services System"; Academic Emergency Medicine vol. 11, No. 5; 604; Abstract from 2004 Society of Academic Emergency Medicine Annual Meeting May 16-19, 2004.

Aufderheide et al.; "Incomplete Chest Wall Decompression during CPR"; Academic Emergency Medicine vol. 11, No. 5; 562; Abstract from 2004 Society of Academic Emergency Medicine Annual Meeting May 16-19, 2004.

Williams et al.; "A Comparison of Traditional Dispatcher-assisted CPR to Compressions-only Dispatcher-assisted CPR"; Academic Emergency Medicine vol. 11, No. 5; 562-563; Abstract from 2004 Society of Academic Emergency Medicine Annual Meeting May 16-19, 2004.

Min et al.; "Clinical Factors Have Time-dependent Influences on Death Rate after Cardiac Arrest"; Academic Emergency Medicine vol. 11, No. 5; 563; Abstract from 2004 Society of Academic Emergency Medicine Annual Meeting May 16-19, 2004.

Lerner et al.; "Geographic Variability of Out-of-hospital Cardiac Arrest after Controlling for Population Density"; Academic Emergency Medicine vol. 11, No. 5; 563; Abstract from 2004 Society of Academic Emergency Medicine Annual Meeting May 16-19, 2004.

Nichol et al.; "A Controlled Study of the Cost-Effectiveness of Emergency Medical Services for Out-of-hospital Cardiac Arrest: An Economic Evaluation of the OPALS Study"; Academic Emergency Medicine vol. 11, No. 5; 603; Abstract from 2004 Society of Academic Emergency Medicine Annual Meeting May 16-19, 2004.

Stiell et al.; "Are Any ALS Treatments Associated with Better Survival in Out-of-hospital Cardiac Arrest"; Academic Emergency Medicine vol. 11, No. 5; 524; Abstract from 2004 Society of Academic Emergency Medicine Annual Meeting May 16-19, 2004.

Hall et al.; "A Randomized Controlled Trial Comparing the Efficacy of Training Paramedic Students Endotracheal Intubation on a Patient Stimulator vs. Human Subjects"; Academic Emergency Medicine vol. 11, No. 5; 492; Abstract from 2004 Society of Academic Emergency Medicine Annual Meeting May 16-19, 2004.

Stiell et al.; "Predictors of Survival for Out-of-hospital Chest Pain Patients in the OPALS Study"; Academic Emergency Medicine vol. 11, No. 5; 586; Abstract from 2004 Society of Academic Emergency Medicine Annual Meeting May 16-19, 2004.

Khalid et al.; "Location of Out-of-hospital Cardiac Arrests to Determine Placement of AED"; Academic Emergency Medicine vol. 11, No. 5; 589; Abstract from 2004 Society of Academic Emergency Medicine Annual Meeting May 16-19, 2004.

Denny et al.; "Socioeconomic Status and Survival after Out-of-hospital Cardiac Arrest"; Academic Emergency Medicine vol. 11, No. 5; 590-591; Abstract from 2004 Society of Academic Emergency Medicine Annual Meeting May 16-19, 2004.

De Maio et al.; "The Epidemiology of Cardiac Arrest in Schools: Limited Potential fo PAD in a Low-risk Setting"; Academic Emergency Medicine vol. 11, No. 5; 607; Abstract from 2004 Society of Academic Emergency Medicine Annual Meeting May 16-19, 2004.

Wirtz et al.; "Rate and Outcomes of Unrecognized Esophageal Placement of Endotracheal Tubes by Paramedics in an Urban Emergency Department"; Academic Emergency Medicine vol. 11, No. 5; 591-592; Abstract from 2004 Society of Academic Emergency Medicine Annual Meeting May 16-19, 2004.

Weiss et al.; "An Automatic Transport Ventilator (ATV) vs. Bag Valve Mask (BVM) for Ventilation during EMS Transport"; Academic Emergency Medicine vol. 11, No. 5; 592; Abstract from 2004 Society of Academic Emergency Medicine Annual Meeting May 16-19, 2004.

Gerein et al.; "What is the Etiology of Out-of-Hospital Pediatric Cardiopulmonary Arrest?"; Academic Emergency Medicine vol. 11, No. 5; 437; Abstract from 2004 Society of Academic Emergency Medicine Annual Meeting May 16-19, 2004.

Chng et al.; "Pediatric Emergency Airway Management"; Academic Emergency Medicine vol. 11, No. 5; 438-439; Abstract from 2004 Society of Academic Emergency Medicine Annual Meeting May 16-19, 2004.

Guidelines 2000 for Cardiopulmonary Resuscitation and Emergency Cardiovascular Care; Supplement to Circulation; vol. 102, No. 8, Aug. 22, 2000; pp. I-98 and I-100-I-102.

Wang et al., "Preliminary Experience with a Prospective, Multi-centered evaluation of Out-of-hospital Endotracheal Intubation"; Resuscitation 58; 2003; pp. 49-58.

Wright et al.; "Acute Endotracheal Tube Occlusion Caused by Use of an Esophageal Detector Device: Report of a Case and a Discussion of Its Utility"; Annals of Emergency Medicine; vol. 43, No. 5; 626-629; May 2004.

Katz et al.; "Misplaced Endotracheal Tubes by Paramedics in an Urban Emergency Medical Services System"; Annals of Emergency Medicine; vol. 37, No. 1; 32-37; Jan. 2001.

U.S. Appl. No. 11/180,912, filed Jul. 14, 2005.

Aase et al.; "CPR Artifact Removal from Human ECG Using Optical Multichannel Filtering"; EEE Transactions on Biomedical Engineering; vol. 47, No. 11; 1440-1449; Nov. 2000.

Eilevstjønn et al.; "Multichannel Adaptive Filtering Using an Efficient Matching Pursuit-Like Algorithm for Removal of CPR Artifacts in ECG Signals"; ICASSP 2002; pp. 1-4; May 13-17, 2002.

Wik et al.; "Quality of Cardiopulmonary Resuscitation During Out-of-hospital Cardiac Arrest"; American Medical Association; vol. 293, No. 3; 299-304; Jan. 2005.

Wik et al., "Quality of Bystander Cardiopulmonary Resuscitation Influences Outcome after Prehospital Cardiac Arrest "; Resuscitation 28; 1994; pp. 195-203.

Van Hoeyweghen et al., "Quality and Efficiency of Bystander CPR"; Resuscitation 26; 1993; pp. 47-52.

Gallagher et al., "Effectiveness of Bystander Cardiopulmonary Resuscitation and Survival Following Out-of-hospital Cardiac Arrest "; American Medical Association; vol. 274, No. 24; Dec. 1995; pp. 1922-1925.

L.A. Geddes et al, "Principles of Applied Biomedical Instrumentation", Third Edition, Wiley Interscience (1989), pp. 571-573.

Jouni Nurmi et al., "Adherence to Guidelines When Positioning the Defibrillation Electrodes", Resuscitation vol. 61, (2004), pp. 143-147.

Luis A. Pagan-Carlo, MD et al, "Transthoracic Defibrillation: Importance of Avoiding Electrode Placement Directly on the Female Breast", vol. 27, No. 2, pp. 449-452, JACC (1996).

F. Lateef et al., "Chest Impedance: Characteristics of Local Patients", Singapore Med. J. vol. 41(7), pp. 331-334, (2000).

Jo Kramer-Johansen et al., "Transthoracic Impedance Changes as a Tool to Detect Malpositioned Tracheal Tubes", vol. 76, pp. 11-16, Resuscitation, (2008).

Klemens W. Kohler et al, "Detection of Malintubation Via Defibrillator Pads", vol. 77, pp. 339-344, Resuscitation (2008).

* cited by examiner

07:22 under US 7,774,054 B2 — page 1–2

METHOD AND SYSTEM TO DETERMINE CORRECT TUBE PLACEMENT DURING RESUSCITATION

This invention relates to a system and method for determining if a tracheal tube or similar is in a correct position during resuscitation.

BACKGROUND OF THE INVENTION

Tracheal intubation is one of several methods to secure the airway during resuscitation, being used especially when a protected airway is lacking. An example of guidelines for performing this is described on pages I-98-1-102 in Guidelines 2000 for Cardiopulmonary Resuscitation and Emergency Cardiovascular Care.

Tracheal intubation is considered a difficult skill in general; See Wang et al "Preliminary experience with prospective, multi-centered evaluation of out-of-hospital endotracheal intubation" Resuscitation 58 (2003) 49-58. Insufficiently trained providers may cause complications to the victim during the procedure. The following complications are seen: Trauma to oropharynx, ventilation withheld for unacceptably long periods, delayed or withheld chest compressions, esophageal or right mainstem bronchial intubation, failure to secure the tube and failure to recognize misplacement of the tube.

One study by Wirtz et al, "Rate and Outcomes of Unrecognized Esophageal Placement of Endotracheal Tubes by Paramedics in an Urban Emergency Department", Academic Emergency Medicine Volume 11, Number 5 591-592, found that esophageal intubation occurs in 10% of the cases, and right mainstem intubation occurs as frequently as in 18% of the cases. Esophageal intubation is associated with poor outcome, since lung ventilation is inhibited for extended periods of time.

Even with a correctly placed tube, tube dislodgement may happen while the patient is moved. In Wang et al 22 incidents of tube dislodgement were reported out of 742 intubated patients. Dislodgement is related to poorly securing of the tube, and may not be recognized by the paramedics.

The standard method for determining tube placement is auscultation. This is a difficult skill which needs regular practice to be sensitive. In the pre-hospital setting it is often complicated due to noise and motion.

End tidal $CO_2$ detectors are also used, but this technique is not well suited for patients in cardiac arrest. Esophageal detector devices are also used. This is a balloon or syringe that is connected to the tube after intubation. The idea is that air can not be retracted from a tube in the esophagus. This is a separate device that represents extra cost and the procedure prevents compressions and ventilation from being delivered. Furthermore, there have been incidents where a esophageal detector device has sucked mucus into the tube, thereby falsely indicating wrong tube placement and preventing use of the tube. There is also a risk that vomit has entered the airways before intubation, and that vomit can occlude the tube, resulting in false positive detection from the esophageal detector device.

SUMMARY OF THE INVENTION

It is an object of this invention to provide a method and a system which can provide reliable indications of tube positioning without the abovementioned disadvantages, and which also may be incorporated in existing life saving equipment, such as defibrillators.

It is known that impedance measurements may provide information about living tissue. This is usually performed by positioning electrodes on or in the body and applying a varying voltage or current through the electrodes. The impedance measurements with two or more electrodes are per se known to a person skilled in the art, and examples of such measuring systems are described in U.S. Pat. No. 4,540,002, U.S. Pat. No. 5,807,270 and WO 2004/049942. As described in the latter publication the impedance can be measured in chosen depths by using a number of electrodes.

In WO2004/004541 Wik describes a system using electrodes applied externally to the chest of a patient and being connected to a near constant current source. Also connected to the electrodes is a measuring unit comprising an instrument amplifier, low pass filter and a precision rectifier. Fundamental to the solution described in this publication is the measurement of a reference value ZO. This measurement ZO represents one observation of the impedance between the electrodes while the patient is not breathing. A problem related to this solution is that the impedance is not constant but depends on the time from the application of the electrode, the weight of the person and electrode positions. It is an object of this invention to provide a solution that gives reliable measurements under such varying conditions.

The system proposed according to the invention provides an alternative method and system for controlling the positioning of the tube by using a plurality of electrodes attached to the patients thorax for measuring breathing movements. Such electrodes and measuring systems are known from other application, like the solution described in EP 1157717, measuring parameters for use in relation to a defibrillator and providing feedback to the user of the equipment thus helping him to perform the CPR, and EP 1057498, for measuring blood circulation using electrodes attached to the patients skin.

An object of this invention is thus to provide means for improving positioning of a tracheal tube by monitoring the breathing movements of the patient during tracheal tube positioning. The means are based on impedance measurements of the body.

The above-mentioned objects may be obtained by a method for controlling insertion of a tracheal tube in a patient comprising the steps of: positioning at least two electrodes on the patient's chest, said electrodes being coupled to a measuring instrument for measuring the impedance between the electrodes, measuring the impedance variation while ventilating the patients lungs, e.g. using mask ventilation, and generating and storing in a microcomputer a first data set representing the typical variation without intubation Zm, inserting the tube into the trachea, measuring the impedance variation while ventilating the patient's lungs with the tube inserted therein and generating a second data set representing the typical variation with intubation Zt, and evaluating, e.g., by the microcomputer determining a difference between the first and second data sets wherein the difference represents the change in impedance with and without the tube inserted, and based on this evaluation the microcomputer generating a signal(s) being indicative of the difference between the sets. The above-mentioned objects are also obtained by a system for controlling insertion of a tracheal tube in a patient, comprising at least two electrodes adapted to be coupled to the patient's chest for providing impedance measurements, a measuring instrument, e.g., including a microcomputer, for performing the impedance measurement, said instrument also being provided with storage means for storing a first data set representing chosen characteristics of the impedance change during a first measurement, and evaluation means, e.g., the microcomputer, for comparing the first data set with a second data set representing the characteristics of a second impedance measurement, for evaluating the difference between said measurements and providing an evaluation signal, said first and second data sets representing impedance variations measured during lung inflation with and without an inserted tracheal tube.

When combined with other life saving equipment there is a problem in that such activities as chest compressions may affect the impedance, thus making the measurements more difficult to read. According to a preferred embodiment, the invention comprises the use of adaptive filtering of the kind described in EP 1073310 for removing these artifacts, the adaptive filtering also being per se known to a person skilled in the art.

BRIEF DESCRIPTION OF THE INVENTION

The invention will be described below with reference to the accompanying drawings, illustrating the invention by way of examples.

DETAILED DESCRIPTION OF THE INVENTION

Figure 1:
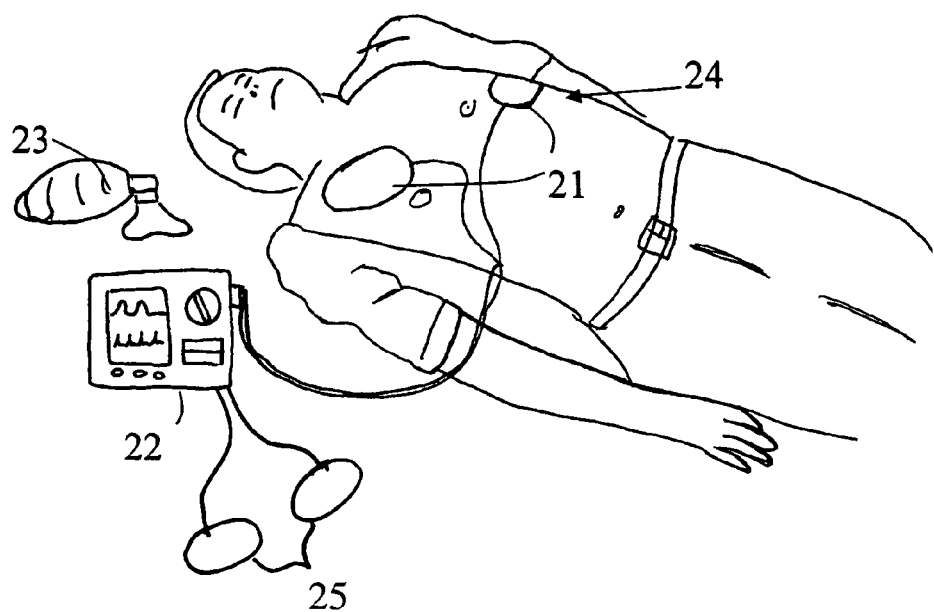
FIG. 1 illustrates a patient on which the invention is used.

The system according to the invention, illustrated in FIG. 1 comprises at least two electrodes 21 attached to the patient's thorax 24, an impedance measurement system connected to the electrodes, a microcomputer connected to the impedance measurement system and a display unit connected to the microcomputer, all arranged within a processing unit 22.

Figure 2:
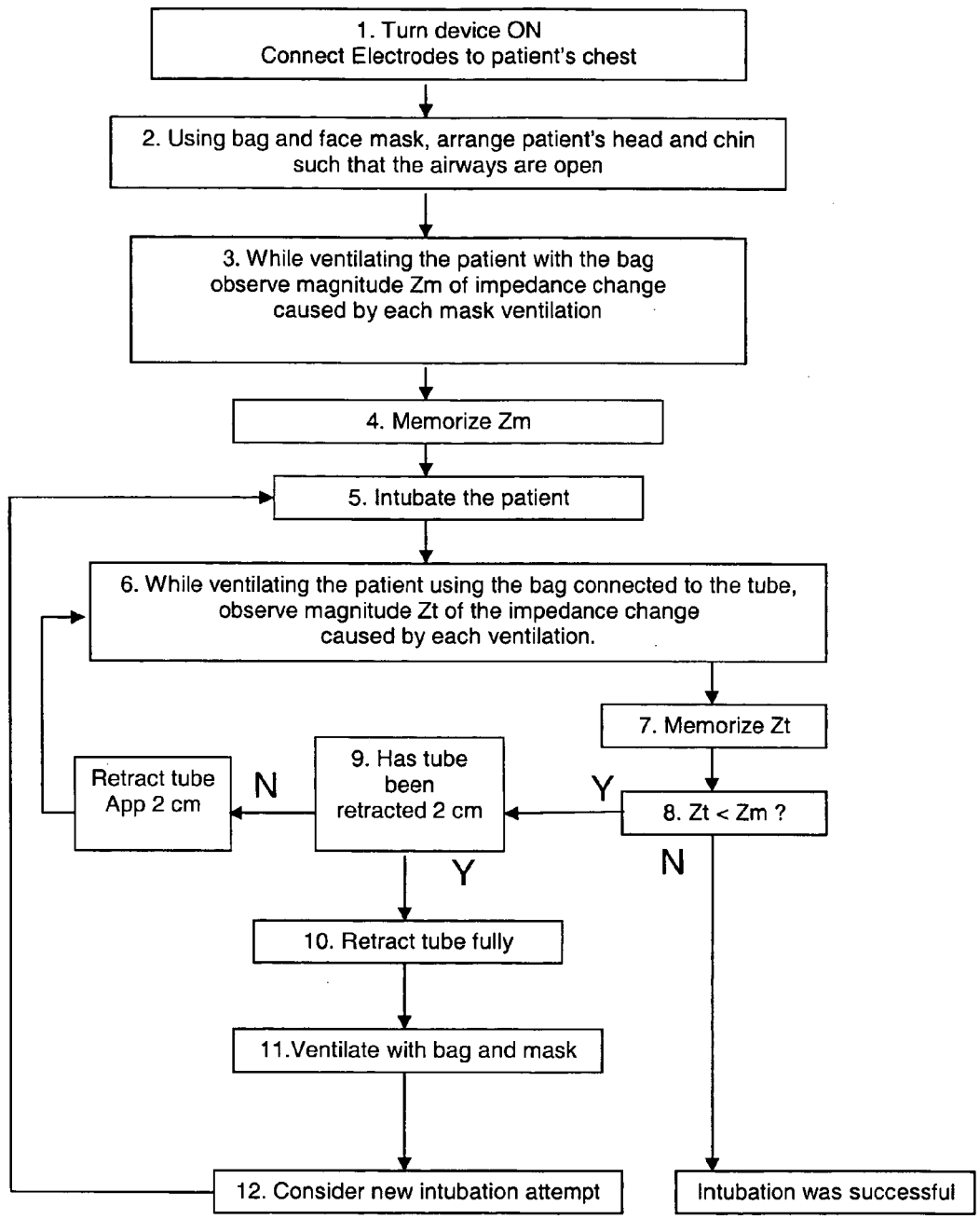
FIG. 2 shows a schematic diagram of the preferred method according to the invention.

The processing unit 22 illustrated may be provided with visual or acoustic means for providing feedback to the user, e.g. instructing the user in the same way as described in EP 1215993 to retract or adjust the position of the tube or simply be triggering an acoustic warning signal Referring to FIG. 2 the device according to a preferred embodiment of the invention, is adapted to be used according the following steps:

1. Turn device ON. Connect electrodes 21 to patient's chest 24.
2. Using bag and face mask 23, arrange patients head and chin such that airways are open.
3. While ventilating the patient with the bag and while mask leakage is negligible, observe magnitude of impedance change caused by each mask ventilation.
4. Memorize the magnitude of the typical impedance change caused by mask ventilation Zm.
5. Intubate the patient.
6. While ventilating the patient using the tube, observe the magnitude of the impedance change caused by each intubated ventilation.
7. Memorize the typical magnitude of the impedance change caused by each intubated ventilation Zt
8. Compare Zm with Zt. If Zt=>Zm, conclude that intubation was successful.
9. If Zt<Zm, consider the possibility of right mainstem intubation. Retract the tube about 2 cm and repeat from step 6.
10. If Zt<Zm still, retract the tube fully.
11. Ventilate the patient using bag and mask.
12. Consider repeating the intubation procedure from step 5 on.

Figure 3:
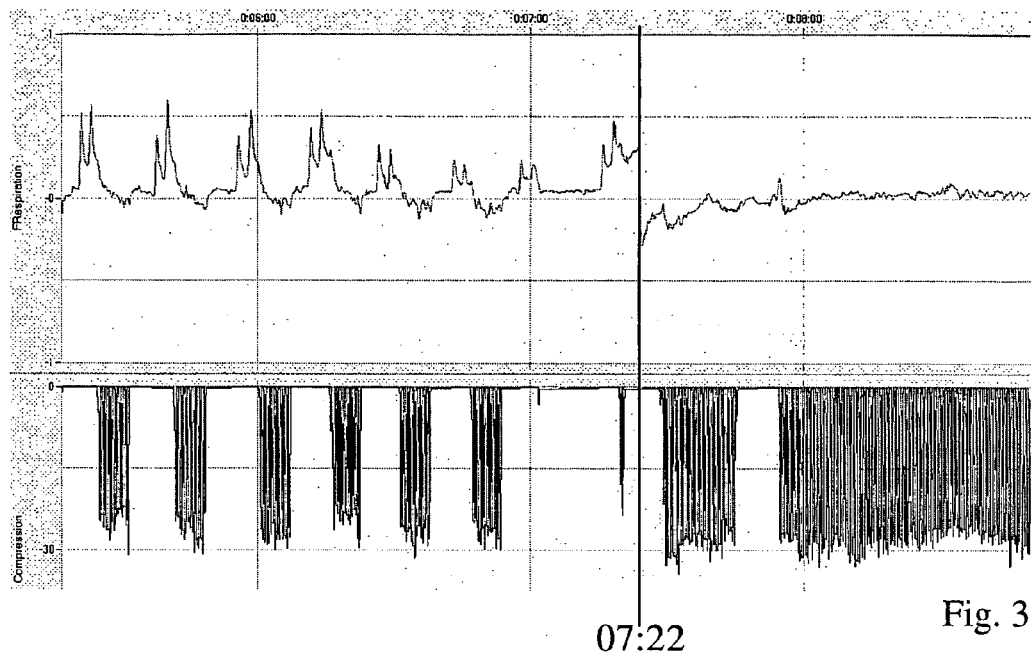
FIG. 3 illustrates measurements in a situation where the tube is misplaced.
Figure 4:
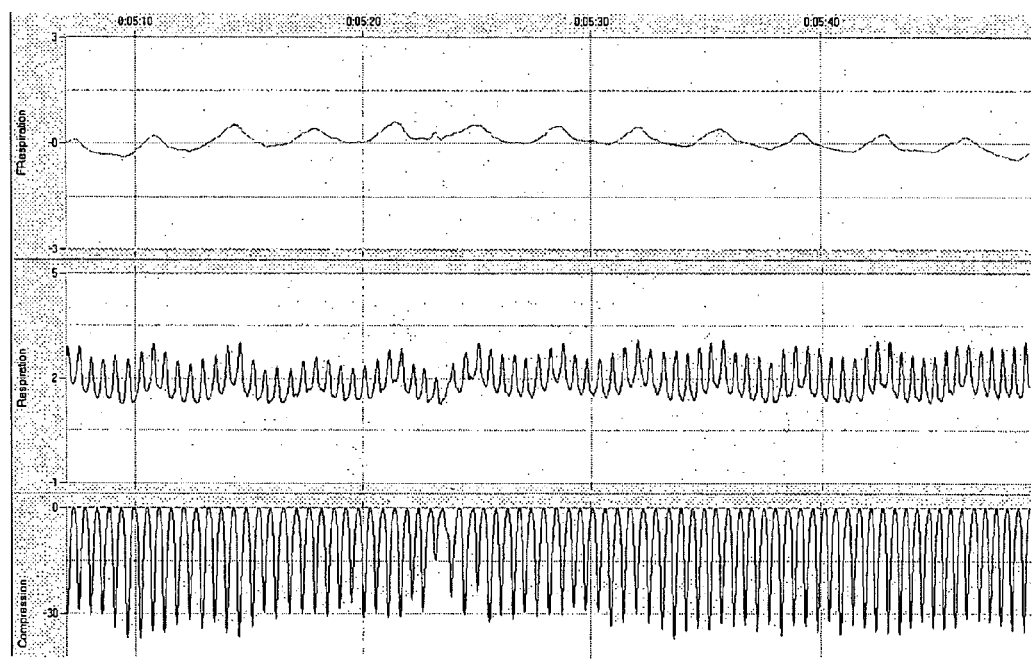
FIG. 4 illustrates the signal filtering according to a preferred embodiment of the invention.
Figure 5:
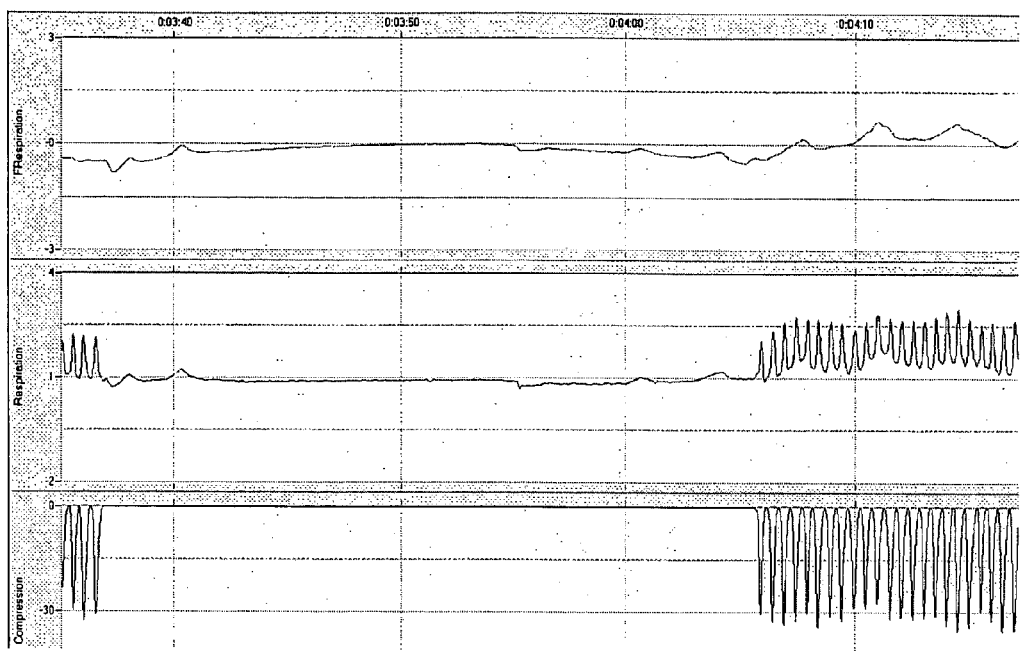
FIG. 5 illustrates measurements indicating a successful intubation.

Typical impedance variations when the patient is ventilated with a standard bag are 0.5-1.0 OHM, but some body types deviate from this norm. Large bodies may be as low as 0.5 Ohm, and small bodies may be more than 1 Ohm. Mechanical conditions related to lungs and chest may also give deviations, this including lung edema, lung cancer, trauma, drowning, foreign elements, etc. Illustrations showing examples of impedance variations are shown in FIGS. 3, 4 and 5, which will be described more in detail below.

Zt and Zm may be represented by a single number representing the typical impedance change in each situation, e.g. the mean amplitude in a certain time window. More thorough statistical analysis may also be used providing a larger set of values representing Zt and Zm, such as standard deviation etc.

According to one embodiment of the invention the system is incorporated is an external defibrillator. The advantage of such an embodiment is cost, space and time saving. A defibrillator is normally arranged with a plurality of electrodes 25 attached to the patient's thorax (schematically shown in FIG. 1 next to the patient), an impedance measuring system connected to the electrodes, a microcomputer connected to the impedance measurement system and a display unit connected to the microcomputer. Hence, integrating the technology is a matter of design.

Typical design characteristics of the system: Electrodes are arranged on the thorax preferably over both lungs. The impedance measurement system has a resolution of 10 milliohm. Dynamic range of the measurement system is from 0 ohm to 250 ohm, when typical defibrillator electrodes are used. The impedance measurement system uses a near constant AC current of 0.1 to 3 mA, and the AC frequency is typically in the range of 30 kHz to 200 kHz.

The processing unit 22, e.g., a microcomputer, can be arranged to memorize the impedance change of step 4 and 7, and to facilitate, e.g., perform, the comparisons of Zm and Zt of steps 8-10. The microcomputer can also be arranged to fully guide the user through the steps 1-12, using audible prompts, text, pictograms, video or any combination of audible and visible guiding.

One other embodiment is a stand-alone unit arranged to just facilitate intubation support and ventilation support. Such a stand-alone unit can be further expanded to facilitate CPR feedback (see EP 1157717), using a chest compressions sensor (EP 1057451) and other sensors that describe how CPR is performed and how the patient responds to the CPR. Patient response to CPR can be determined using ECG analysis (EP 1215993) and end tidal $CO_2$ measurements.

Confirmation of tube placement can also be done during chest compressions, provided that the system is expanded with an adaptive filter for example a digital adaptive filter, the principle of which is detailed in EP 1073310, which is included here by way of reference. In this application, however, it is the compression artifact on the impedance signal that is filtered, using a signal from a chest compression sensor as reference input. This filter may take into account different types of measurements done during chest compressions, such as the measured movements of the chest, applied pressure or acceleration of a sensor positioned on the chest.

By measuring these parameters, the effects of the chest compressions may be filtered out from the impedance signal so as to obtain control of the intubation by calculating the maximum correlation between a reference signal, e.g. a signal obtained without chest compressions, and the measured signal.

FIG. 3 show traces of impedance changes (top) and chest compressions depth (bottom). The two ventilations in between the series of 15 compressions are evident in the beginning of the figure as twin peaks in the respiration signal. Here ventilations were delivered using face mask and bag. Intubation was performed at time 07:22, and after that the impedance signal disappears. Hence, $Zm<Zt$, and misplaced tube is indicated. As indicated in FIG. 2 the tube may then be retracted or removed.

FIG. 4 show traces of digital adaptive filtered impedance waveform (top), the corresponding impedance raw signal (middle), and the chest compression depth waveform (bottom). The ventilations are evident in the top trace. Chest compressions cause artifacts in the impedance raw signal, which are effectively removed by the digital adaptive filter.

FIG. 5 shows an example of successful intubation: The top and middle trace show two ventilations (Zm) followed by a long pause when intubation is performed. Then ventilations and chest compressions resume. We can see that the magnitude of the impedance signal after intubation Zt is greater than Zm.

Although the invention described above is mainly aimed at automated recognition and comparing of the stored impedance data the comparison may be performed manually by inspecting the curves, such as illustrated in FIGS. 3-5, during the operation. The stored data is then kept sufficiently long to enable the user to see excerpts of both the data with and without the inserted tube.

Also, the invention is described using only two electrodes, but more than two electrodes may also be used according to the invention, e.g. for more precisely measuring of impedance at a chosen depth, e.g. for reducing disturbances from the skin impedance.

The invention claimed is:

1. Method for controlling insertion of a tracheal tube in a patient comprising the steps of:
    positioning at least two electrodes on the patient's chest, said electrodes being coupled to a measuring instrument for measuring the impedance between the electrodes,
    measuring an impedance variation while ventilating the patient's lungs without the tube inserted in the patient, and generating and storing a first data set representing the impedance variation without intubation Zm,
    inserting the tube into the trachea of the patient,
    measuring an impedance variation while ventilating the patient's lungs with the tube inserted therein and generating a second data set representing the impedance variation with intubation Zt, and
    evaluating the first (Zm) and second (Zt) data sets representing the change in impedance variation with and without the tube inserted, and based on this evaluation generating a signal being indicative of the difference between the sets.

2. Method according to claim 1, wherein said evaluation signal is a feedback to the user, indicating the need for retracting or adjusting the tube position.

3. Method according to claim 2, wherein each Zt and Zm is constituted by a single number representing the typical impedance change in each situation, and wherein the evaluation signal is a warning signal if $Zt<Zm$.

4. Method according to claim 1, wherein said evaluation comprises the use of an adaptive filter.

5. Method according to claim 4, wherein the intubation is performed during chest compressions, said adaptive filter being adapted to filter out the chest compression artifacts in the impedance signal.

6. System for controlling insertion of a tracheal tube in a patient, comprising:
    at least two electrodes adapted to be coupled to the patient's chest for providing impedance measurements,
    a measuring instrument for performing impedance measurements, said instrument also being provided with storage means for storing first and second data sets each representing an impedance variation determined from the impedance measurements, wherein the first data set represents an impedance variation Zm and the second data set represents an impedance variation Zt, and the measuring instrument measures (1) the impedance variation Zm occurring while the patient's lungs are ventilated without the tube inserted in the patient's lung and generating and storing the first data set representing the impedance variation Zm and (2) the impedance variation Zt occurring while ventilating the patient's lungs with the tube inserted therein and generating the second data set representing the impedance variation Zt, and
    evaluation means for comparing the first data set with the second data set, for determining a difference between said impedance variation Zm and said impedance variation Zt, and providing an evaluation signal based on the difference.

7. System according to claim 6, wherein said evaluation means comprises a display providing a visual representation of the data sets graphically as curves on a screen for manual evaluation of the difference between the the impedance variation Zm and the impedance variation Zt.

8. System according to claim 6, wherein said first data set represents a mean amplitude of measurements of Zm occurring while the patient's lungs are ventilated without the tube inserted, and said second data set represents a mean amplitude of measurements of Zt occurring while the patient's lungs are ventilated with the tube inserted, and said evaluation means is adapted to compare these mean amplitudes.

9. System according to claim 6, further comprising acoustic or visual means for providing a warning signal based on the evaluation signal.

10. System according to claim 6, being integrated in a defibrillator.

11. A method for determining an impedance variation associated with an insertion of a tracheal tube in a patient comprising:
    positioning at least two electrodes on a chest of the patient, said electrodes coupled to an electronic device measuring an impedance between the electrodes;
    measuring with the electronic device a first variation Zm in the impedance while ventilating the patient when the tube is not inserted in the patient, and storing in a memory of the electronic device a first data set representing Zm;
    inserting the tracheal tube into the trachea of the patient and ventilating the patient;
    measuring with the electronic device a second variation Zt of the impedance while ventilating the lungs with the tube inserted and storing in the memory a second data set representing Zt, and
    generating by the electronic device a signal indicative of a comparison of Zm and Zt.

12. The method of claim 11 further comprising the electronic device generating:

an output signal indicating that the tracheal tube was properly inserted if the signal indicates that Zt is at least as large as Zm, and an output signal indicating that the tracheal tube was not properly inserted if the signal indicates that Zm is greater than Zt.

13. The method of claim 11 wherein the first data set includes a single value for Zt representing a mean of measurements of the first variation in the impedance, and the second data set includes a single value for Zt representing a mean of measurements of the second variation in the impedance.

14. Method according to claim 1 further comprising applying an adaptive filter of the electronic device to filter out chest compression artifacts in the impedance signal during chest compressions of the patient.

15. An electronic instrument comprising:

at least two electrodes adapted to be coupled to a chest of the patient;

an impedance measuring system coupled to the electrodes and measuring impedances across the electrodes, while the electrodes are applied to the chest;

a memory storing data regarding impedances;

a processor receiving signals indicating measured impedances from the impedance measuring system and accessing the memory, the processor is programmed to:

generate data regarding impedance variations in the measured impedances and store in memory data representing an impedance variation Zm occurring while the patient is ventilated without the tube inserted in the patient and data representing an impedance variation Zt occurring while the patient is ventilated with the tube inserted in the patient, and compare the data representing the impedance variation Zm to the data representing the impedance variation Zt, and generate a evaluation signal based on the comparison.

16. The electronic instrument of claim 15 wherein the processor is further programmed to generate a first output signal indicating that the tracheal tube was properly inserted if the comparison indicates that impedance variation Zt is at least as large as impedance variation Zm, and a second output signal indicating that the tracheal tube was not properly inserted if the signal indicates that impedance variation Zm is greater than impedance variation Zt, and the instrument further comprises a display for presenting an representation of the first and second output signals.

17. The electronic instrument of claim 15 wherein the data representing an impedance variation Zt represents a mathematical mean of measurements of the first variation in the impedance, and the data representing an impedance variation Zt represents a mathematical mean of measurements of the second variation in the impedance.

18. The electronic instrument of claim 15 further comprising an adaptive filter adapted to filter out chest compression artifacts in the impedances measured across the electrodes.

19. The electronic instrument of claim 15 wherein the system is included in an external defibrillator.

20. The electronic instrument of claim 15 further comprising a source of alternating current applied to the electrodes, wherein the applied alternating current is in a range of 0.1 milliamperes (mA) to 3 mA.

* * * * *